United States Patent
Hu

(12) United States Patent (10) Patent No.: US 9,146,197 B2
Hu (45) Date of Patent: Sep. 29, 2015

(54) METHOD AND APPARATUS FOR DETERMINING PHASE FRACTIONS OF MULTIPHASE FLOWS

(75) Inventor: Jin-lin Hu, Shildon (GB)

(73) Assignee: Taylor Hobson Limited (GB)

( * ) Notice: Subject to any disclaimer, the term of this patent is extended or adjusted under 35 U.S.C. 154(b) by 719 days.

(21) Appl. No.: 13/257,433

(22) PCT Filed: Mar. 11, 2010

(86) PCT No.: PCT/GB2010/050433
§ 371 (c)(1),
(2), (4) Date: Sep. 19, 2011

(87) PCT Pub. No.: WO2010/106354
PCT Pub. Date: Sep. 23, 2010

(65) Prior Publication Data
US 2012/0111124 A1 May 10, 2012

(30) Foreign Application Priority Data
Mar. 20, 2009 (GB) .................................. 0904758.0

(51) Int. Cl.
*G01F 1/74* (2006.01)
*G01N 22/00* (2006.01)
*G01N 22/04* (2006.01)
(Continued)

(52) U.S. Cl.
CPC .............. *G01N 22/00* (2013.01); *G01N 22/04* (2013.01); *G01N 22/005* (2013.01); *G01R 27/04* (2013.01); *G01R 27/2658* (2013.01)

(58) Field of Classification Search
CPC ..... G01N 22/00; G01N 22/005; G01N 22/04; G01R 27/2658; G01R 27/04; G01F 1/74

USPC ........................................... 324/636, 634, 633
See application file for complete search history.

(56) References Cited

U.S. PATENT DOCUMENTS

| | | | | |
|---|---|---|---|---|
| 3,458,808 A | * | 7/1969 | Agdur | 324/633 |
| 4,571,544 A | * | 2/1986 | Walton | 324/636 |
| 4,943,778 A | * | 7/1990 | Osaki | 324/636 |

(Continued)

FOREIGN PATENT DOCUMENTS

| | | |
|---|---|---|
| GB | 2 120 791 A | 12/1983 |
| WO | 00/43759 A1 | 7/2000 |

(Continued)

OTHER PUBLICATIONS

Stobie, G. et al., "Dualstream II Advanced Wet Gas Meter-Flow Testing at CEESI,"7th South East Asia Hydrocarbon Flow Measurement Workshop, Mar. 5-7, 2008.

(Continued)

*Primary Examiner* — Jermele M Hollington
*Assistant Examiner* — Christopher McAndrew
(74) *Attorney, Agent, or Firm* — Lerner, David, Littenberg, Krumholz & Mentlik, LLP

(57) ABSTRACT

A multiphase meter for use in the quantification of the individual phase fractions of a multiphase flow has: a resonant cavity through which, in use, a multiphase fluid flows, a signal generator configured to apply electromagnetic energy at a range of frequencies to the cavity, and an enhancing and/or suppressing facility for enhancing and/or suppressing resonant modes of a signal produced resultant to the application of electromagnetic energy to the cavity.

19 Claims, 4 Drawing Sheets

Fig. 2

Figure 1:
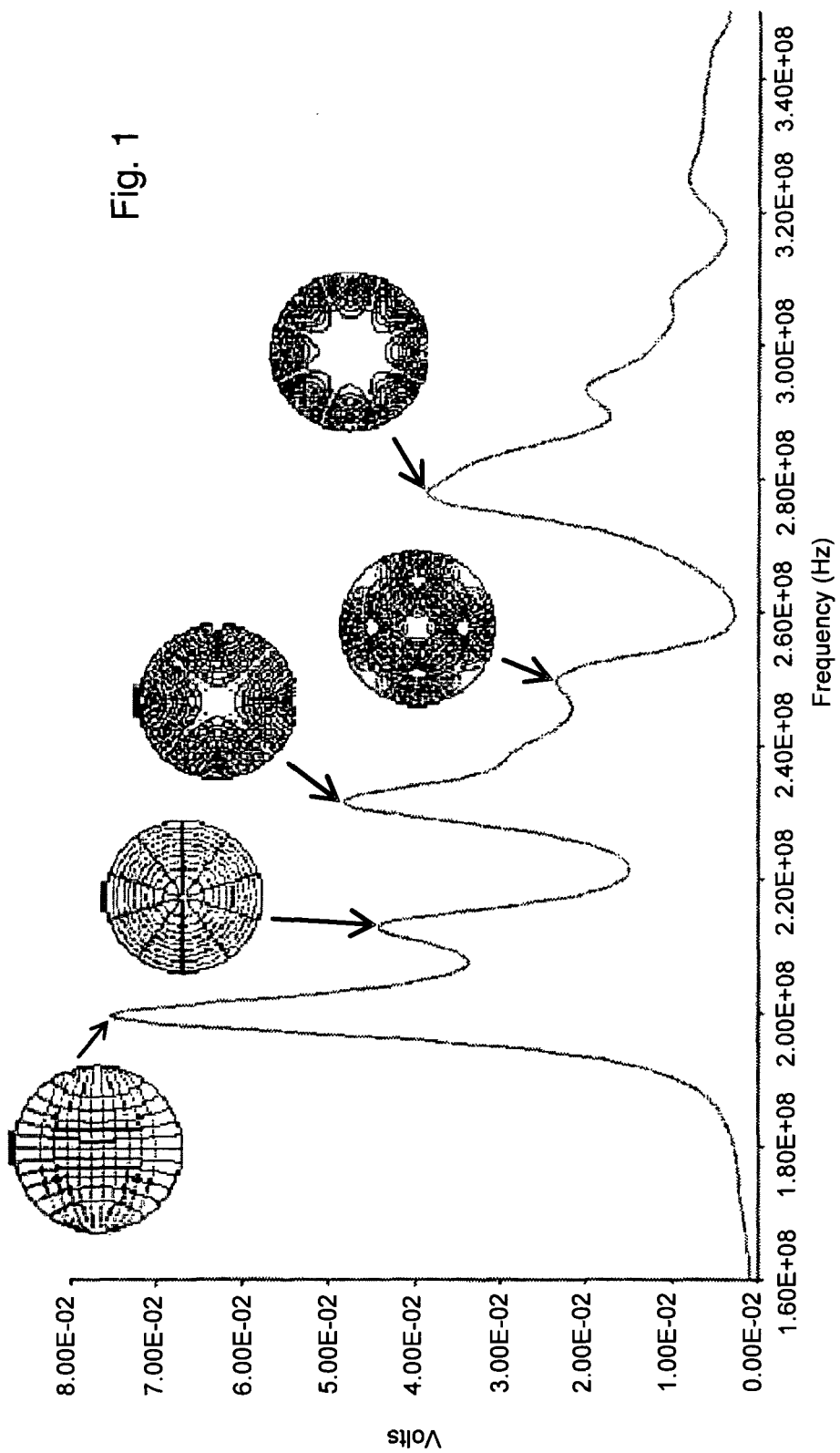

(51) Int. Cl.
  *G01R 27/26* (2006.01)
  *G01R 27/04* (2006.01)

(56) References Cited

U.S. PATENT DOCUMENTS

| | | | |
|---|---|---|---|
| 5,103,181 | A | 4/1992 | Gaisford et al. |
| 5,793,216 | A | 8/1998 | Constant |
| 6,771,080 | B2 * | 8/2004 | Conrads et al. ............... 324/636 |
| 6,915,707 | B2 | 7/2005 | Nyfors et al. |
| 6,954,077 | B2 * | 10/2005 | Strang ............................ 324/636 |
| 7,982,469 | B2 * | 7/2011 | Jakkula et al. ................. 324/633 |
| 2004/0085077 | A1 | 5/2004 | Nyfors |
| 2007/0279073 | A1 | 12/2007 | Wee |
| 2008/0211516 | A1 * | 9/2008 | Jakkula et al. ................. 324/634 |

FOREIGN PATENT DOCUMENTS

| | | | |
|---|---|---|---|
| WO | WO 0043759 A1 * | 7/2000 | |
| WO | 02/16931 A1 | 2/2002 | |

OTHER PUBLICATIONS

De Leeuw, R. et al., "Paper 21: liquid correction of Venturi meter readings in wet gas flow," North Sea Flow Measurement Workshop, 1997.

Re Van Maanen, H, "Paper 7.3: Measurement of the Liquid Water Flow Rate Using Microwave Sensors in Wet-Gas Meters: Not As Simple As You Might Think," 26th Int'l North Sea Flow Measurement Workshop, Oct. 21-24, 2008.

Wee, A.,"Paper 1.3: A Combined Multiphase and WetGas Meter with In-Situ Measurement of Fluid Properties," The Americas Workshop, Apr. 27-29, 2010.

Wilie, S.R. et al.,"RF sensor for multiphase flow measurement through an oil pipeline," Measurement Sci, and Tech. IOP publishing UK, vol. 17, No. 8, Jul. 13, 2006.

Gibbons, R.M. et al., "An Equation of State for Polar and Non-Polar Substances and Mixtures," J.Chem.Soc., Faraday Trans. 2, 80, 1019-1038, 1984.

"Handbook of Multiphase Flow Metering," published by the Norwegian Society for oil and gas measurement, rev. 2, Mar. 2005.

Collins, Alistair et al., "The Development of and Initial Data from a New Multiphase Wet Gas Meter," 28th Int'l North Sea Flow Measurement Workshop, Oct. 26-29, 2010.

Collins, Alistair et al.,"The Development of and Initial Data from a New Multiphase Wet Gas Meter," 10th South East Asia Hydrocarbon Flow Measurement Workshop, Mar. 8-10, 2011.

Tudge, M. et al., "The Development of and Initial Data from a New Multiphase Wet Gas Meter," The Americas Workshop, Apr. 26-28, 2011.

International Search Report, PCT/GB2010/050433, dated Jul. 28, 2010.

* cited by examiner

METHOD AND APPARATUS FOR DETERMINING PHASE FRACTIONS OF MULTIPHASE FLOWS

The present application is a national phase entry under 35 U.S.C. §371 of International Application No. PCT/GB2010/050433 filed Mar. 11, 2010, published in English, which claims priority from United Kingdom application GB 0904758.0, the entire contents of which are hereby incorporated by reference.

This invention relates to a multiphase meter and has been devised, in particular, to provide a method and apparatus which can be used in the quantification of the individual phase fractions flowing from a hydrocarbon well. More particularly, though not necessarily exclusively, the invention is concerned with providing a method and apparatus which can be applied in the determination of the water fractions in gas/water or gas/condensate/water streams.

The output from an oil/gas well typically comprises a number of liquid/gas components. The liquid typically comprises a mixture of water and liquid hydrocarbons (i.e. condensate). The water component can be saline.

For various reasons, the fractions of the individual phases within a multiphase flow need to be determined; and determined with considerable accuracy. Historically, flows have been separated in a mechanical separator and each flow component measured individually. This is no longer deemed satisfactory and there is a growing demand for continuous in-line real time measurements.

A variety of instruments have been developed in an attempt to quantify, on a continuous basis, the respective fractions of gas, liquid hydrocarbon and water. One general approach involves transmitting electromagnetic (EM) energy through a section of a multiphase flow and analysing the subsequent affect on the properties of the electromagnetic waves due to the various phase fractions of the flow.

There are a number of types of electromagnetic multiphase meter. In one approach, the attenuation of the incident energy is measured. An example of an instrument of this type is described in U.S. Pat. No. 5,793,216.

Another approach has been to relate the fluid composition to electromagnetic wave phase shift between transmitted and received electromagnetic energy or between receivers placed at different locations. An example of this type of instrument is described in published US Patent Application 2007/0279073.

In yet another approach, the flow is passed through a resonant cavity. Electromagnetic resonant sensors utilize the electromagnetic resonance principle to measure the complex permittivity of materials. It is well known that wavelengths and energy losses of electromagnetic waves are dependent on the complex permittivity of the dielectric material through which the waves are propagating. Resonant frequencies and quality factors of a resonant cavity can vary with the change of the complex permittivity of the material within the cavity. Since the complex permittivity of water differs significantly from that of gas, oil or condensate, electromagnetic resonant-based measurements are well suited to the accurate determination of water in a hydrocarbon flow. An example of a multiphase meter employing a resonant cavity sensor is described in U.S. Pat. No. 6,915,707.

According to one aspect, the invention comprises a method of determining phase fractions in a multiphase flow, said method including the steps of: passing said multiphase flow through a resonant cavity; subjecting multiphase flow in said cavity to electromagnetic energy over a range of frequencies; and deriving an indication of individual phase fractions of the multiphase flow from an observation of the change of resonant characteristics of said electromagnetic energy due to said flow, said method further including suppressing at least one resonance mode within said cavity.

Advantageously, this can enable resonance peaks from a wide variety of gas volume fractions (GVFs) and flow states to be readily discriminated, and thus accurate phase fractions to be determined, even when highly saline water is present.

Preferably said method further includes locating resonance-mode altering structures within said resonant cavity.

Preferably said resonant cavity has a non-conducting material therein, said method comprising embedding said resonance-mode altering structures within said non-conducting material.

In one aspect the invention provides apparatus for use in determining individual phase fractions in a multiphase flow, said apparatus including: a resonant cavity through which, in use, a multiphase fluid flows; and a signal generator configured to apply electromagnetic energy at a range of frequencies to said cavity; said apparatus further including a suppression facility operable to suppress at least one resonance mode within said resonant cavity.

Preferably said suppression facility comprises one or more physical structures located within said cavity.

Preferably said cavity includes a non-conducting material, said physical structures being embedded within said material.

According to one aspect, there is provided apparatus for use in determining individual phase fractions in a multiphase flow, said apparatus comprising: a resonant cavity through which, in use, a multiphase fluid flows; and one or more probes operable to apply electromagnetic energy at a range of frequencies to said cavity; said apparatus further comprising a suppression or enhancement facility arranged to suppress or enhance at least one resonance mode within said resonant cavity.

In one aspect, the invention comprises a method of determining phase fractions in a multiphase flow in which one of said phases comprises saline water, said method including the steps of: passing said multiphase flow through a resonant cavity; whilst in said cavity, subjecting said multiphase flow to electromagnetic energy over a range of frequencies; and deriving an indication of individual phase fractions of the multiphase flow from an observation of the change of resonant characteristics of said electromagnetic energy due to said flow, said method including enhancing at least one resonance mode within said cavity.

Preferably said method further includes suppressing at least one resonance mode within said cavity.

Preferably said method involves locating physical structures within said cavity to enhance and/or suppress selected resonance modes.

Many variations in the way the present invention can be performed will present themselves to those skilled in the art. The description which follows is intended as an illustration only of means of performing the invention and any lack of description of variants or equivalents should not be regarded as limiting. Wherever possible, a description of a specific element should be deemed to include any and all equivalents thereof whether in existence now or in the future.

Figure 2:
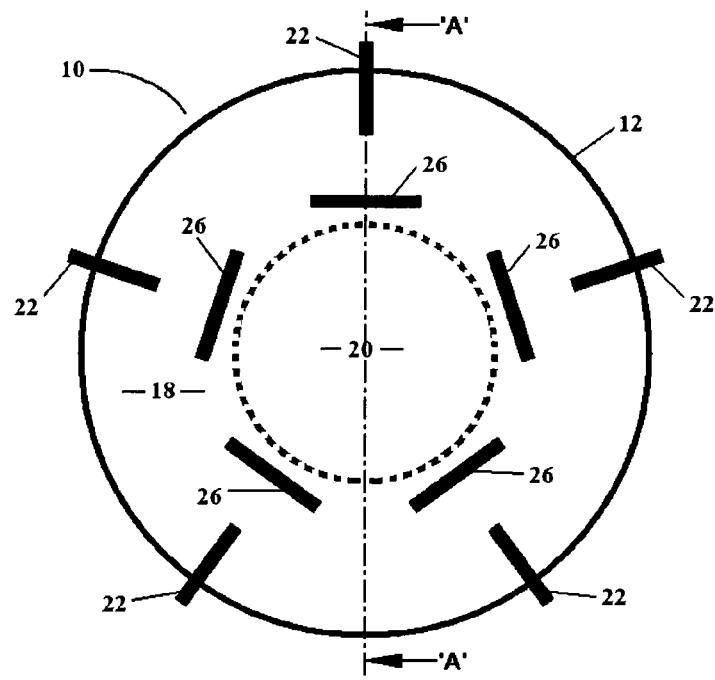
Figure 3:
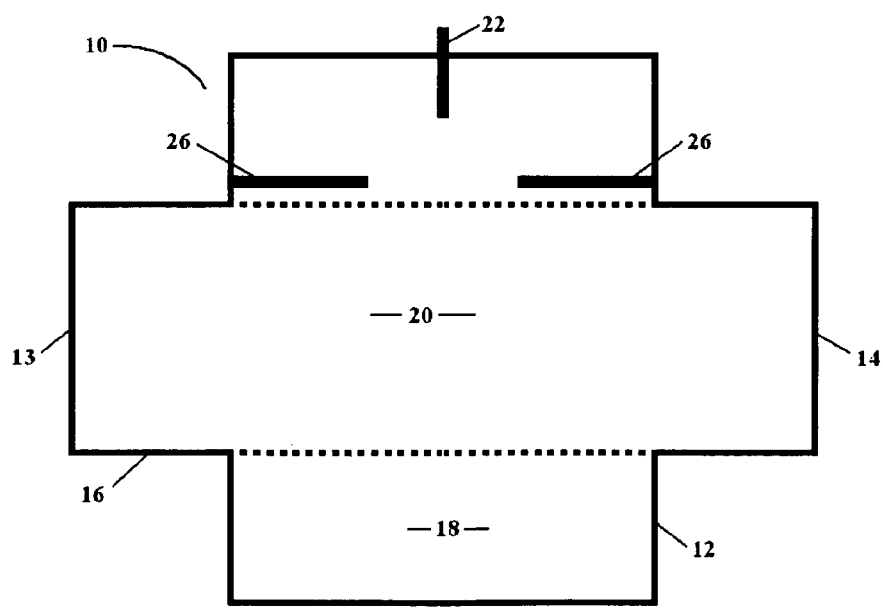
Figure 4:
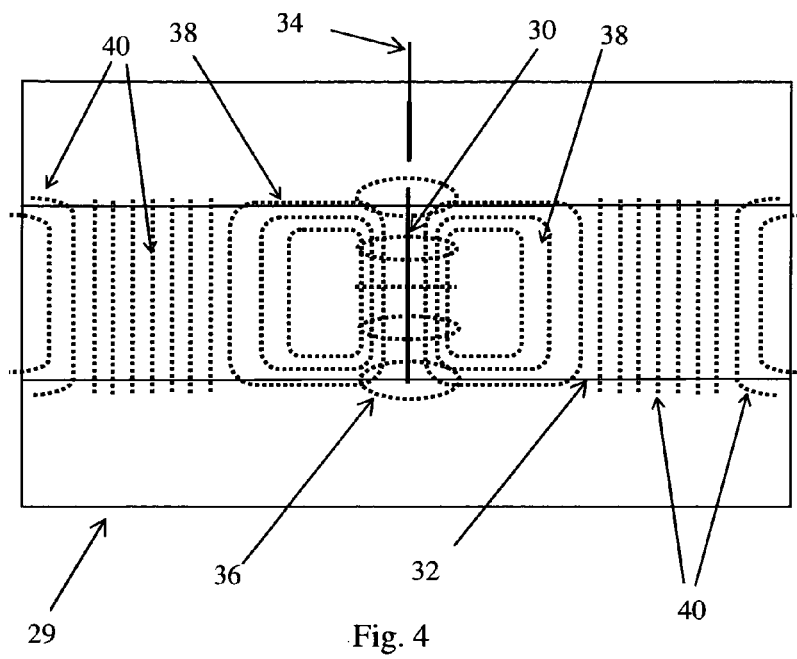
Figure 5:
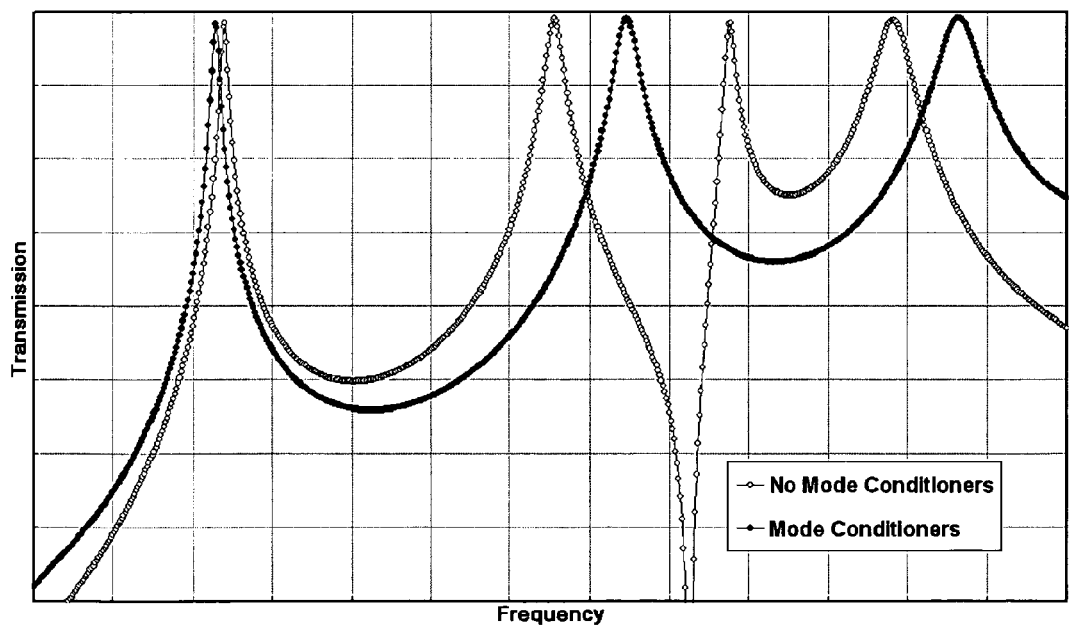
Figure 6:
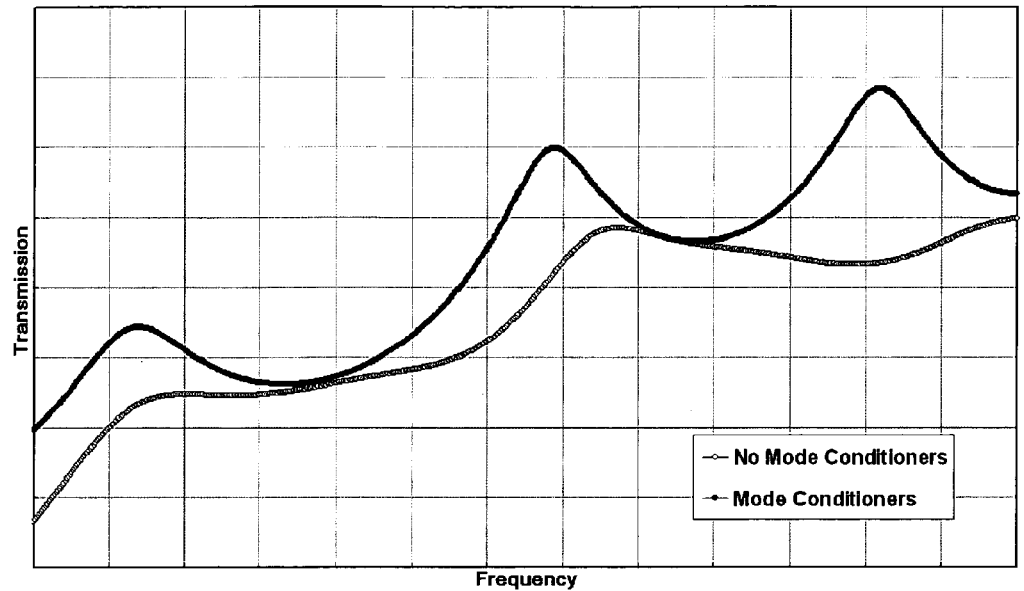
Figure 7:
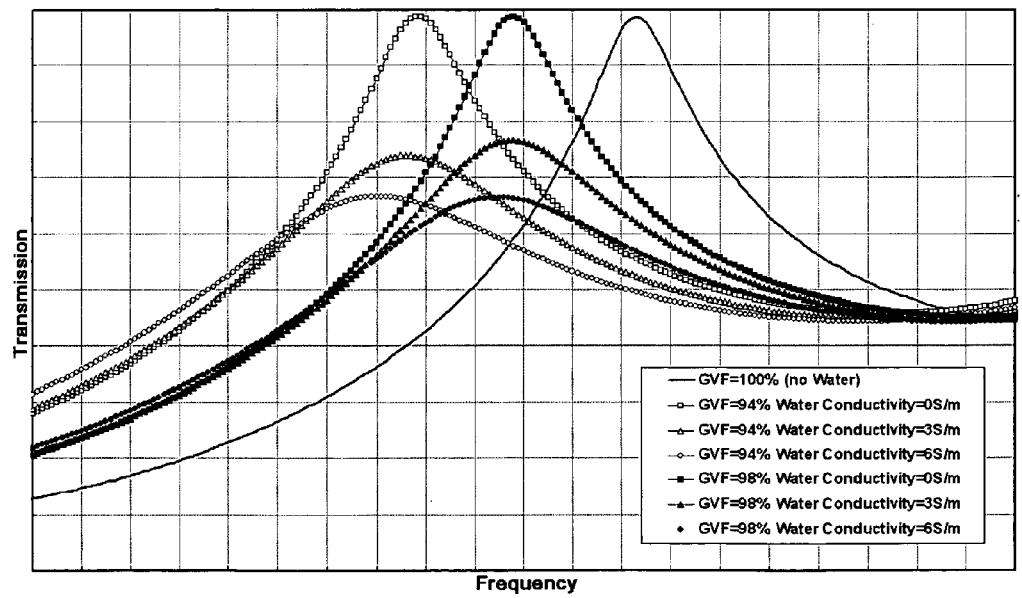

Examples of the invention will now be described with reference to the accompanying drawings in which:

FIG. 1: shows an example received signal plotted against frequency for a cylindrical resonant cavity;

FIG. 2: shows a schematic end cross-sectional view through a measurement apparatus;

FIG. 3: shows a view along the line 'A'-'A' in FIG. 2;

FIG. 4: shows a longitudinal cross-section through a cavity having an annular mode conditioner;

FIG. 5: shows a comparison of frequency traces derived from a gas-only flow through a resonant cavity not provided with resonance-mode altering structures, and one provided with resonance-mode altering structures;

FIG. 6: shows a comparison of frequency traces derived from a salt water/gas annular flow through a resonant cavity not provided with resonance-mode altering structures, and one provided with resonance-mode altering structures; and FIG. 7: shows results measured using a resonant cavity provided with resonance mode altering structures, for water/gas flows with different gas volume fractions (GVFs) and different water conductivities.

There is described herein a method of, and apparatus for, use in the quantification of phase fractions within a multiphase flow. Examples of multiphase flows include output streams from oil/gas wells which typically include mixtures of liquids and gases. The liquids, in turn, typically comprise a mixture of liquid hydrocarbons and water.

A principle of operation for electromagnetic fraction meters is to electrically enclose the material being measured within a cavity so as to create a cavity with high quality factors at desired modes and low quality factors at undesired modes. At most frequencies, electromagnetic waves will propagate into the cavity and reflect back and forth a number of times until they are entirely dissipated. However, at certain, resonant, frequencies, the continuously reflecting waves repeatedly continuously interfere with one another in such a way as to lead to a steady state of high intensity and low intensity regions that are spread across the volume of the cavity. Accordingly, when a range of frequencies are applied to the cavity, the received signal will have peaks (modes) at each of the resonant frequencies.

Different types of field may exist within a resonant cavity including transverse electric (TE), transverse magnetic (TM), and transverse electromagnetic (TEM) fields. At resonant frequencies, standing waves of these fields are created and a pattern of the fields is established that is dependent upon the frequency of operation and the permittivity of the materials flowing through the cavity. As the resonant frequency is approached, the measured signal will rapidly increase in intensity, FIG. 1 shows an example received signal plotted against frequency for a cylindrical resonant cavity; next to each of the modes is shown a diagrammatic representation of the electromagnetic wave energy pattern for the corresponding mode.

Theoretically, for RF/EM-based sensing devices there are an infinite number of resonance modes that occur throughout the frequency spectrum for any electromagnetic resonant cavity. Undesired modes can make it difficult to discern the useful modes by merging with them or obscuring them completely as they respond to changes in the phase fractions of multiphase flows.

The $TE_{111}$ mode occupies the lowest frequency of the resonance modes and is a suitable mode for the measurement of water. However, the inventor has observed that, when the water is not pure or fresh, for example if the water is saline, the lower frequency modes may be obscured thereby making it difficult, or impossible, to use them for measurement.

The inventor has appreciated that the high conductivity of salt water—the conductivity of seawater at 20° C. is about 5 Siemens/m—contributes to obscuration of the lower frequency modes as electromagnetic waves propagating through salt water at radio and microwave frequencies lose a significant amount of their energy to the salt water.

Referring now to FIGS. 2 and 3, apparatus 10 is provided for determining individual phase fractions within a multiphase flow, the apparatus 10 having a resonant cavity 12. As can be seen the resonant cavity 12 is defined around a section of pipe 16 between an inlet 13 and an outlet 14 and is configured so that the multiphase flow can pass, without disturbance, through the resonant cavity. Mounting flanges (not shown) may be provided about the inlet and outlet to simplify the task of mounting the apparatus in a flow line.

The outer walls defining the resonant cavity 12 and the pipe section 16 are preferably formed from steel or another, mechanically strong, conductive material. The walls are configured to withstand the environmental conditions experienced in the vicinity of oil/gas wellheads.

Completely filling the cavity region about the pipe 16 is non-conducting material 18. Whilst the material 18 could be formed from a variety of materials including gases, and liquids such as transformer oil, given the pressures and nature of the outputs from an oil/gas well, the material 18 preferably comprises a bulk ceramic material. It is preferable that the complex-permittivity of the material 18 has the smallest possible dependency on temperature.

In this example, the ceramic material is annular in form, the inner diameter defining a through bore 20 which coincides with the inner diameter of the pipe section 16. A person skilled in the art will appreciate that the ceramic material may have other forms and that the pipe need not have a circular cross-sectional profile.

As well as smoothly directing the flow through the resonant cavity 12, the ceramic material 18 serves other purposes. The ceramic acts as protection for at least one and, as shown in FIG. 2, five RF probes 22. In the form shown these probes are equally spaced around a circumference of the cavity 12 and can be simple monopole probes. The probes may be mounted in suitable sockets formed in the outer wall of the cavity, but project into the ceramic material 18. Being effectively embedded with the ceramic material 18, the probes 22 are thus physically remote from the multiphase fluid flowing through the apparatus.

The probes 22 are included in an emitting/receiving circuit which allows each probe to function as an emitter or receiver of electromagnetic energy as is well known to those skilled in the art.

For the apparatus of FIG. 2, resonance modes within the cavity are altered to enhance the quality of phase fraction measurement. Generally, resonance modes exist across the electromagnetic spectrum starting from the fundamental frequency. However some of the modes present can interfere with the measurements of useful modes as they respond to changes in the phase fractions of the multiphase flow.

Preferably, when one of the phases is saline water, with introduction of mode conditioners at least one resonance mode within the cavity is enhanced.

Thus, undesired modes may be suppressed and/or enhanced to create clear frequency windows within which only selected resonance modes are present. This, in turn, enables the selected modes to be observed and tracked for a variety of multiphase flows.

The alteration of resonance modes whether by way of suppression or enhancement, is preferably effected by the use of physical structures located within the resonant cavity 16. In the particular case described herein, resonance-mode altering structures (hereinafter called mode conditioners) 26 are provided. As can be seen, these comprise members mounted about the x-axis through the bore 20. It is convenient to embed the mode conditioners within the ceramic material 18. The configuration of the mode conditioners can vary according to the availability of materials and the resonance modes of interest or not. Simple flat plate conditioners contained within the ceramic material 18 are illustrated in FIGS. 2 and 3 but the mode conditioners may extend around an arc of the cavity, may be flush with the bore 20, and/or could be part or fully: rectangular, circular, annular, arched, spherical, cylindrical, ovoidal, toroidal, saw-toothed, sinusoidal, castellated, leaf-shaped, etc., or any combination of the above. Preferably the mode conditioners are located within the cavity.

To operate in the manner described, the mode conditioners 26 are formed from a highly conductive material, preferably having properties that approach those of a perfect electric conductor. It is well-known that there is no tangential total electric field on the surface of a perfect electric conductor. Accordingly, placement of a mode conditioner within a resonant cavity introduces a new cavity boundary or a new mode conditioner boundary condition causing the tangential components of the electric fields and the surface of the mode conditioner to disappear. Excitation by way of an RF probe also causes currents to flow within the mode conditioner thereby initiating electromagnetic fields. A consequence of the mode conditioner being within the resonant cavity is that the properties of at least some of the resonance modes within the cavity change.

Computer-aided optimization can be used to establish the dimensions, position and shape of the mode conditioner (or mode conditioners as the case may be), according to design requirements, to arrive at one or more structures which either suppress or enhance the resonance modes of choice.

FIG. 4 shows a longitudinal cross-section through a resonant cavity 29 having an annular mode conditioner 30 (shown in phantom lines) disposed coaxially about the longitudinal axis of a bore 32 through which a multiphase flow having a saline fraction may pass so as to extend around the bore 32. When RF energy is supplied to the cavity 29 by an RF probe, magnetic loop, 34, this causes a current to flow in the mode conditioner which initiates a magnetic field 36 that is tangential to the mode conditioner 30 thereby allowing electric fields 38 that would otherwise have been suppressed by the presence of salt water to be enhanced (or setup). The initiated magnetic and electric fields also interact with other electric and/or magnetic fields 40 in the cavity 29 thereby altering the resonant characteristics of the cavity 29. In particular, the initiated magnetic field 36 can act to suppress one or more TM modes thereby facilitating modal resolution.

Preferably, the mode conditioners are arranged to suppress TM modes and/or enhance TE modes. Advantageously, TE modes are better defined than TM modes and this can facilitate measurement. In contrast, TM modes, in particular, appear to suffer relatively high attenuation in the presence of saline water even without mode-conditioners.

Turning now to FIG. 5, traces are shown of the resonance modes arising from a gas-only flow through a resonant cavity, with and without mode conditioners. A gas-only flow (GVF=100%) is used for reasons of clarity. Without mode conditioners, four resonance peaks are present with the second, third and fourth peaks being close to one another. In comparison, when mode conditioners are incorporated within the cavity, the third peak is suppressed and the remaining peaks are widely spaced thereby enhancing discrimination between the peaks and thus improving measurement.

FIG. 6 illustrates a comparison when the flow through the cavity is a salt-water/gas annular flow with a GVF of 90%. Without mode conditioners, the resonance peaks are almost completely attenuated. However, with the inclusion of mode conditioners, all three peaks are significantly reinforced or enhanced and can thus be clearly distinguished.

Turning now to FIG. 7, experimental results are shown of water/gas flows of different GVFs and different water conductivities. In all cases the data is derived using a cavity with mode conditioners. As can be seen, an uncluttered frequency window is obtained within which peak frequency increases with increasing GVF and, with an increase in water conductivity, peak amplitude reduces and peak width increases.

Extracting the various phase fractions from the measured data may be effected by any technique known to those skilled in the art.

A person skilled in the art will appreciate multiphase flows comprise a plurality of individual phases and may have any number of individual phases—including two.

A person skilled in the art will appreciate that the suppression and/or enhancement of one or more modes described herein may be either relative to one or more other modes or absolute.

The examples described herein have been devised to provide a means of determining water content in 'wet gas' flows, i.e. flows in which gas is the predominant phase. However, it will be appreciated, by those skilled in the art, that the principles of the invention may be applied to an analysis of other multiphase flows.

A person skilled in the art will appreciate that, although FIG. 2 shows five mode conditioners, a single or any number of mode conditioners could instead be employed. A person skilled in the art will appreciate that although the mode conditioners of FIG. 6 are shown disposed about a central axis of the cavity, mode conditioners may be located at any appropriate position within the cavity—including coaxial to the centreline of a bore—and may have any appropriate orientation or configuration.

Various features described above may have advantages with or without other features described above.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. Apparatus for use in determining individual phase fractions in a multiphase flow, said apparatus comprising:
    a resonant cavity having a bore through which, in use, a multiphase fluid flows; and
    one or more probes configured to apply electromagnetic energy at a range of frequencies to said cavity;
    said apparatus further comprising a suppression or enhancement facility arranged to suppress or enhance at least one resonance mode within said resonant cavity, wherein such suppression or enhancement facility comprises one or more mode conditioners arranged around the circumferential periphery of the bore.

2. The apparatus of claim 1, further comprising an electrical enclosure defining said cavity and being arranged to contain said applied electromagnetic energy within said cavity.

3. The apparatus of claim 2, wherein said electrical enclosure is a resonant cavity arranged to contain within said cavity electromagnetic energy at said range of frequencies.

4. The apparatus of claim 1, wherein said suppression or enhancement facility comprises one or more physical structures located within said cavity, the physical structures comprising members mounted about an x-axis through a bore.

5. The apparatus of claim 4, wherein at least a portion of at least one of said one or more physical structures is electrically conductive.

6. The apparatus of claim 1, wherein said cavity includes a non-conducting material, said physical structures being embedded within said material.

7. The apparatus of claim 1, wherein at least a portion of at least one of said one or more physical structures is at least one of: flat, rectangular, circular, annular, arched, spherical, cylindrical, ovoidal, toroidal, saw-toothed, sinusoidal, castellated, and leaf-shaped.

8. The apparatus of claim 1, wherein at least a portion of a surface of at least one of said one or more physical structures is flush with a bore passing through said cavity.

9. Apparatus for use in determining individual phase fractions in a multiphase flow, said apparatus comprising:
 a resonant cavity through which, in use, a multiphase fluid flows; and
 one or more probes configured to apply electromagnetic energy at a range of frequencies to said cavity;
 said apparatus further comprising a suppression or enhancement facility comprising one or more electrically conductive structures extending around an arc of the cavity to suppress or enhance at least one resonance mode within said resonant cavity.

10. The apparatus of claim 9, further comprising an electrical enclosure defining said cavity and being arranged to contain said applied electromagnetic energy within said cavity.

11. The apparatus of claim 10, wherein said electrical enclosure is a resonant cavity arranged to contain within said cavity electromagnetic energy at said range of frequencies.

12. The apparatus of claim 9, wherein said cavity includes a non-conducting material, said physical structures being embedded within said material.

13. The apparatus of claim 9, wherein at least a portion of at least one of said one or more physical structures is at least one of: flat, rectangular, circular, annular, arched, spherical, cylindrical, ovoidal, toroidal, saw-toothed, sinusoidal, castellated, and leaf-shaped.

14. The apparatus of claim 9, wherein at least a portion of a surface of at least one of said one or more physical structures is flush with a bore passing through said cavity.

15. Apparatus for use in determining individual phase fractions in a multiphase flow, said apparatus comprising:
 a resonant cavity;
 a wall within the resonant cavity defining a through bore though which, in use, a multiphase fluid flows; and
 one or more probes configured to apply electromagnetic energy at a range of frequencies to said cavity;
 said apparatus further comprising a suppression or enhancement facility comprising one or more electrically conductive structures embedded in the wall to suppress or enhance at least one resonance mode within said resonant cavity.

16. The apparatus of claim 15, wherein the through bore coincides with an inner surface of a pipeline which carries the multiphase flow.

17. The apparatus of claim 15, further comprising an electrical enclosure defining said cavity and being arranged to contain said applied electromagnetic energy within said cavity.

18. The apparatus of claim 17, wherein said electrical enclosure is a resonant cavity arranged to contain within said cavity electromagnetic energy at said range of frequencies.

19. The apparatus of claim 15, wherein said cavity includes a non-conducting material, said electrically conductive structures being embedded within said material.

* * * * *